(12) United States Patent
Sun et al.

(10) Patent No.: US 9,891,133 B2
(45) Date of Patent: Feb. 13, 2018

(54) STRESS-STRAIN TESTING SYSTEM FOR LARGE-DIAMETER STEEL PIPE PILE OF OFFSHORE WIND TURBINE AND CONSTRUCTION METHOD

(71) Applicant: PowerChina Huadong Engineering Corporation Limited, Hangzhou (CN)

(72) Inventors: Miaojun Sun, Hangzhou (CN);
Mingyuan Wang, Hangzhou (CN);
Zhigang Shan, Hangzhou (CN);
Shengjie Di, Hangzhou (CN); Wenbo Du, Hangzhou (CN)

(*) Notice: Subject to any disclaimer, the term of this patent is extended or adjusted under 35 U.S.C. 154(b) by 0 days.

(21) Appl. No.: 15/622,073

(22) Filed: Jun. 13, 2017

(65) Prior Publication Data
US 2018/0003586 A1    Jan. 4, 2018

(30) Foreign Application Priority Data

Jul. 4, 2016    (CN) .......................... 2016 1 0530059

(51) Int. Cl.
*G01L 1/24*    (2006.01)
*G01M 5/00*    (2006.01)
*G01B 11/16*    (2006.01)

(52) U.S. Cl.
CPC ........... *G01M 5/0058* (2013.01); *G01B 11/18* (2013.01); *G01L 1/242* (2013.01); *G01M 5/0025* (2013.01); *G01B 11/16* (2013.01); *G01N 2203/0069* (2013.01); *G01N 2203/0274* (2013.01); *G01N 2203/0641* (2013.01)

(58) Field of Classification Search
CPC ... G01M 5/0058; G01M 5/0025; G01B 11/18; G01B 11/16; G01N 2203/0641; G01N 2203/0274; G01N 2203/0069; G01L 1/242
USPC .......... 73/800, 862.624, 862.621, 865.8, 760
See application file for complete search history.

(56) References Cited

U.S. PATENT DOCUMENTS

| 5,594,819 | A | * | 1/1997 | Narendran | ............. | G01B 11/18 |
|---|---|---|---|---|---|---|
| | | | | | | 250/227.14 |
| 7,703,331 | B2 | * | 4/2010 | Magne | .................... | E21B 43/01 |
| | | | | | | 73/766 |
| 8,736,821 | B2 | * | 5/2014 | Smith | .................. | G01B 11/165 |
| | | | | | | 356/32 |
| 9,791,335 | B2 | * | 10/2017 | Kwon | ..................... | G01L 1/246 |
| 2006/0045408 | A1 | * | 3/2006 | Jones | ..................... | E21B 17/01 |
| | | | | | | 385/12 |

(Continued)

*Primary Examiner* — Jonathan Dunlap
(74) *Attorney, Agent, or Firm* — Wayne & Ken, LLC; Tony Hom

(57) ABSTRACT

The present invention relates to a stress-strain testing system for a large-diameter steel pipe pile of an offshore wind turbine and a construction method, comprising a steel pipe pile, wherein copper belt type sensor cables are correspondingly welded on both sides of the steel pipe pile along an axis direction; each sensor cable is sequentially covered with an epoxy adhesive, gold foil paper and an angle steel welded on the steel pipe pile centering on the copper belt type sensor cable; a fiber core of each copper belt type sensor cable is transferred into a high-strength armored optical cable by a special fixture and then is led out; and the high-strength armored optical cable is connected with a Brillouin optical fiber demodulator. The present invention is applicable to the field of foundation engineering testing and detection technology.

2 Claims, 2 Drawing Sheets

(56) References Cited

U.S. PATENT DOCUMENTS

| | | | |
|---|---|---|---|
| 2009/0217769 A1* | 9/2009 | Roberts | G01B 11/18 73/800 |
| 2011/0176125 A1* | 7/2011 | Smith | G01B 11/165 356/32 |
| 2013/0034324 A1* | 2/2013 | Laing | G01K 11/32 385/13 |
| 2014/0083197 A1* | 3/2014 | Zadok | H04B 10/071 73/800 |
| 2015/0204743 A1* | 7/2015 | Nieuwland | G01L 9/0076 73/705 |
| 2015/0226622 A1* | 8/2015 | Cheng | G01L 9/0027 73/730 |
| 2016/0216166 A1* | 7/2016 | Kwon | G01B 1/00 |

* cited by examiner

STRESS-STRAIN TESTING SYSTEM FOR LARGE-DIAMETER STEEL PIPE PILE OF OFFSHORE WIND TURBINE AND CONSTRUCTION METHOD

FIELD OF THE INVENTION

The present invention relates to a stress-strain testing system for a large-diameter steel pipe pile of an offshore wind turbine and a construction method, and is applicable to the field of foundation engineering testing and detection technology.

BACKGROUND OF THE INVENTION

With rapid development of economy in China, demands for renewable new energies in industrial production and daily life are increasing. Wind energy as one of the current promising rapid-developing new energies attracts attentions of coastal countries around the world. Vigorous development of offshore wind power is an effective means to solve an energy problem of the energy-deficient coastal countries, including China. Southeastern coastal areas in China have extremely rich marine wind energy resources, have developable wind energy resources three times of land wind energies in China, are closer to an electricity load center, and can more conveniently transmit the offshore wind power to southeastern coastal power-deficient areas. Wind power will meet 17% of electricity demands in China according to *China Wind Power Development Planning Roadmap* 2050 released by the Energy Research Institute of National Development and Reform Commission, so a development space of the offshore wind power in China is large.

At present, foundation forms of offshore wind turbines in China and abroad mainly comprise a single pile foundation, a tripod foundation, a gravity foundation, a floating foundation, a suction barrel foundation and the like, wherein a large-diameter steel pipe pile foundation is widely applied in marine wind power projects due to advantages of simple structure, relatively short manufacturing process, mounting convenience, clear stress and the like. In offshore wind farms built in China, the large-diameter single pile foundation accounts for 75%. A supporting testing and detection system for the large-diameter steel pipe pile can fully monitor deformation, stress and damage of the pipe pile during pile-sinking construction and fan operation. Therefore, the testing and detection system for the marine large-diameter steel pipe pile plays a very important role in ensuring safe operation of foundation engineering. Since marine wind farm foundation engineering will inevitably bear the action of wind, wave, flow, storm surge and other loads in a service period, a load magnitude of a steel pipe pile testing system will be greater than a load of a testing system in a land pipe pile foundation. Meanwhile, due to relatively strong corrosiveness of seawater and submarine formations, the pipe pile and the testing system thereof require more comprehensive corrosion protection.

SUMMARY OF THE INVENTION

A technical problem to be solved by the present invention is to provide a stress-strain testing system for a large-diameter steel pipe pile of an offshore wind turbine and a construction method with respect to the above problems, wherein the stress-strain testing system and the construction method can effectively test deformation and stress of the large-diameter steel pipe pile and are used for solving problems of relatively small load and relatively low anti-corrosion standards in the existing testing technology.

The present invention adopts a technical solution that the stress-strain testing system for the large-diameter steel pipe pile of the offshore wind turbine has a steel pipe pile, wherein copper belt type sensor cables are correspondingly welded on both sides of the steel pipe pile along an axis direction; each sensor cable is sequentially covered with an epoxy adhesive, gold foil paper and angle steel welded on the steel pipe pile by using the copper belt type sensor cable as a center, a fiber core of each copper belt type sensor cable is transferred into a high-strength armored optical cable by a special fixture and then is led out; and the high-strength armored optical cable is connected with a Brillouin optical fiber demodulator.

A construction method of the stress-strain testing system for the large-diameter steel pipe pile of the offshore wind turbine comprises the following steps:

1. marking lines for laying the copper belt type sensor cables on both sides of a steel pipe pile along an axis direction, polishing surfaces of the steel pipe pile along the lines and then cleaning dust;

2. laying the copper belt type sensor cables on polished surfaces of the steel pipe pile, and fixing with an electric welding machine in a fixed-point manner;

3. covering the copper belt type sensor cables with the epoxy adhesive, standing for 24 hours to firmly bond the copper belt type sensor cables and the steel pipe pile, and pasting the gold foil paper on a surface of the epoxy adhesive after the epoxy adhesive is completely cured;

4. welding a piece of angle steel on the surface of the steel pipe pile by using the copper belt type sensor cable as a center.

5. transferring a fiber core in each copper belt type sensor cable into a high-strength armored optical cable with a special fixture and leading out, and connecting the armored cable with a Brillouin optical fiber demodulator, and 6. calibrating a sensor through the Brillouin optical fiber demodulator, obtaining signal transmitting time by measuring a phase difference generated when a signal is transmitted and received, and calculating a length change of the copper belt type sensor cables so as to obtain a stress value of the steel pipe pile.

The present invention has beneficial effects that: the present invention effectively protects the optical fiber cables, allows an operating system to normally operate under the action of wind, wave, storm surge and other large loads, and can resist strong corrosion of seawater and the like.

DETAILED DESCRIPTION OF THE INVENTION

Figure 1:
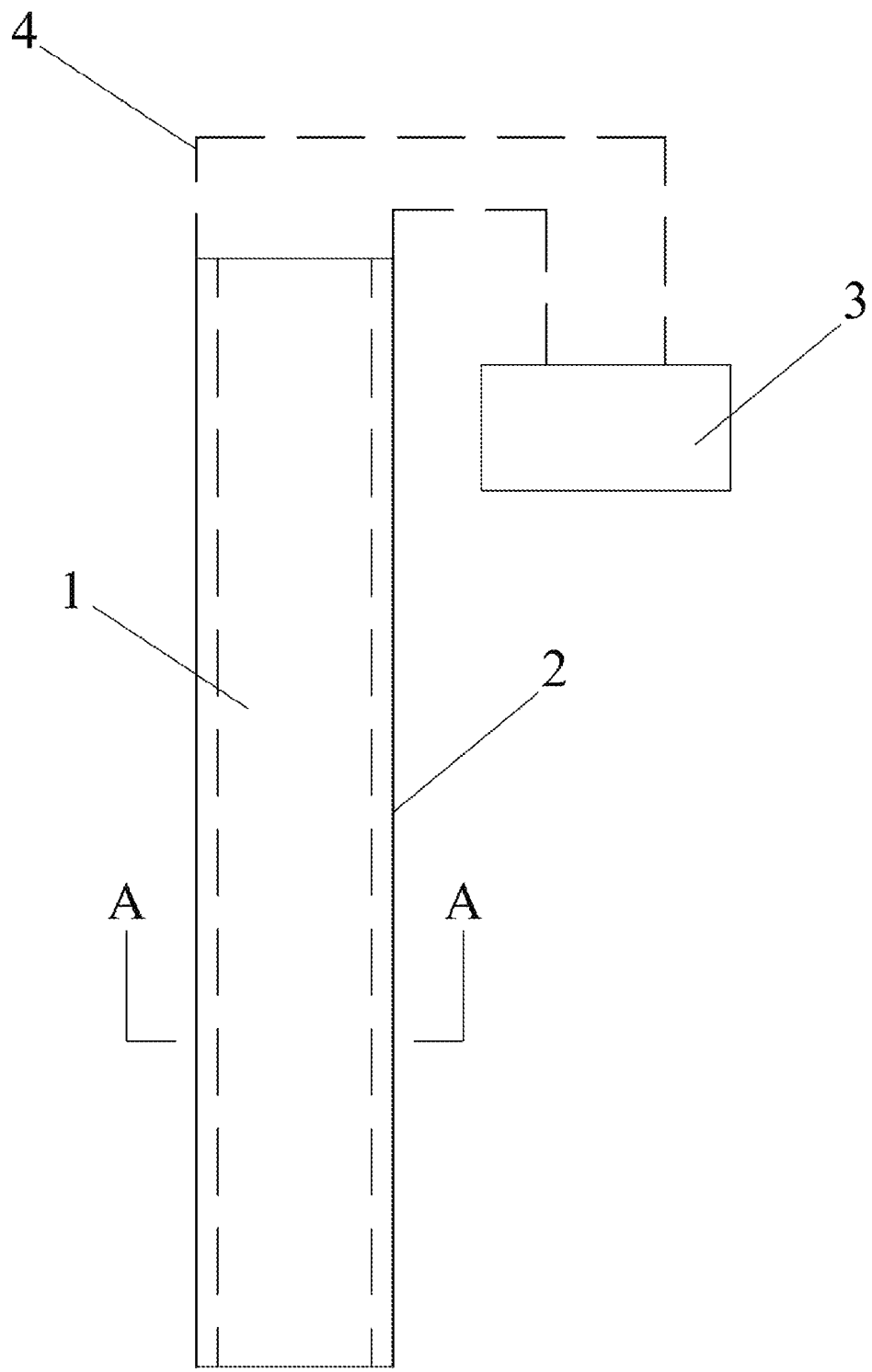
FIG. 1 is a structural schematic diagram of the present invention.
Figure 2:
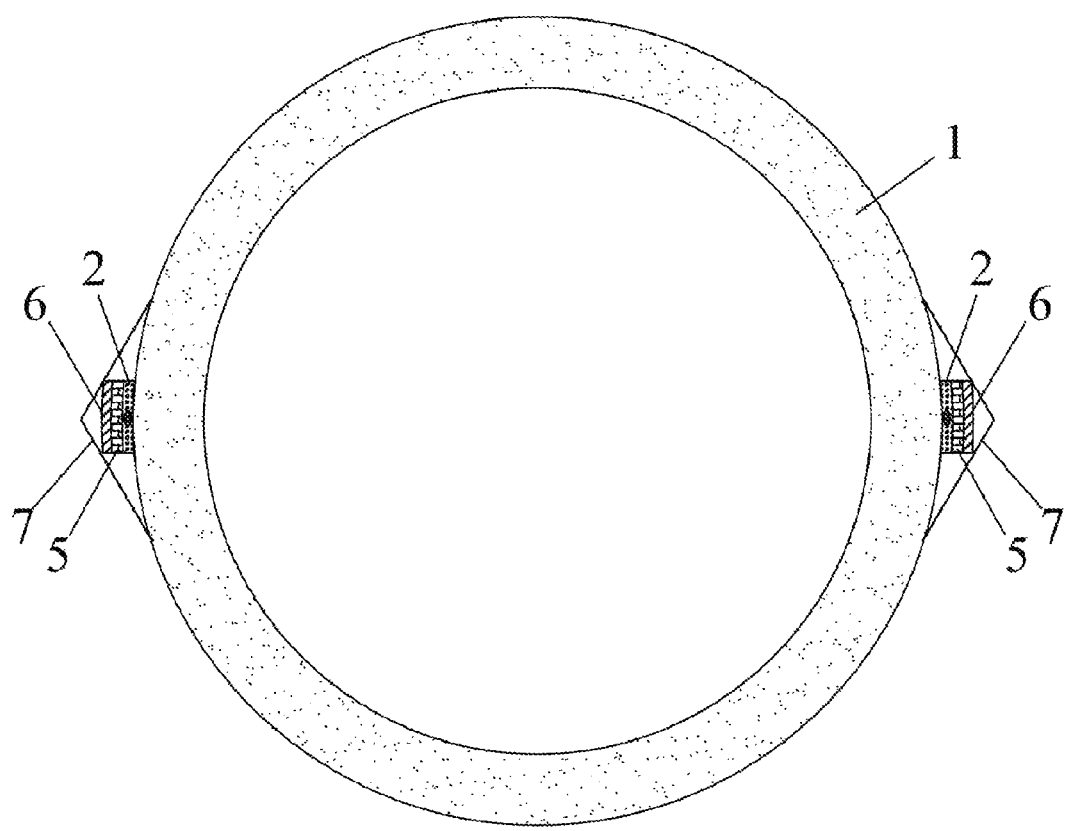
FIG. 2 is a sectional view of A-A in FIG. 1.

As shown in FIG. 1 and FIG. 2, the present embodiment is a stress-strain testing system for a large-diameter steel pipe pile of an offshore wind turbine, wherein the stress-strain testing system has a steel pipe pile 1, copper belt type sensor cables 2 correspondingly welded on both sides of the steel pipe pile 1 along an axis direction, a high-strength armored optical cable 4 transferred from a fiber core 8 in each copper belt type sensor cable 2 with a special fixture, a Brillouin optical fiber demodulator 3 connected with the armored optical fiber, and an epoxy adhesive 5, gold foil paper 6 and angle steel 7 which are sequentially covered on the copper belt type sensor cables 2 for encapsulating and protecting the copper belt type sensor cables 2; and the angle steel 7 is welded on the steel pipe pile 1 by using the copper belt type sensor cable 2 as a center.

A specific implementation method of the present embodiment is as follows:

1. marking lines for laying the copper belt type sensor cables 2 on both sides of a steel pipe pile 1 along an axis direction, polishing surfaces of the steel pipe pile 1 along the lines and then cleaning dust on the steel pipe pile 1, thereby effectively removing rust so that the copper belt type sensor cables 2 can be better welded to the surfaces of the steel pipe pile 1;

2. laying the copper belt type sensor cables 2 on the polished surfaces of the steel pipe pile 1, and fixing with an electric welding machine in a fixed-point manner;

3. covering the copper belt type sensor cables 2 with the epoxy adhesive 5 along the laying lines, standing the epoxy adhesive 5 for 24 hours to completely cure the epoxy adhesive 5 so as to firmly bond the copper belt type sensor cables 2 and the steel pipe pile 1, and pasting the gold foil paper 6 on the surface of the epoxy adhesive 5 for isolation and protection after the epoxy adhesive 5 is completely cured, thereby preventing welding slag produced in subsequent welding work from scalding the copper belt type sensor cables 2;

4. fixing a piece of the angle steel 7 on the surface of the steel pipe pile 1 in a welding manner by using the copper belt type sensor cable 2 as a central line to protect the copper belt type sensor cables 2 and to avoid that the copper belt type sensor cables 2 and protection layers of the epoxy adhesive 5 and the gold foil paper 6 fall off due to dynamic friction force between the pile and soil;

5. transferring a fiber core 8 in each copper belt type sensor cable 2 into a high-strength armored optical cable 4 with a special fixture and leading out; and then connecting the high-strength armored optical cable 4 with a Brillouin optical fiber demodulator 3; and 6. calibrating an optical fiber sensor through the Brillouin optical fiber demodulator 3, wherein the steel pipe pile 1 interacts with surrounding soil during penetration and the steel pipe pile 1 generates axial strain; obtaining signal transmitting time by measuring a phase difference generated when a signal is transmitted and received; calculating a length change of an optical fiber so as to obtain a strain value; solving a pile body stress of the steel pipe pile 1 through the strain based on an elasticity theory; and finally obtaining pile body axial force, lateral friction resistance and pile end resistance.

What is claimed is:

1. A stress-strain testing system for a large-diameter steel pipe pile of an offshore wind turbine, having a steel pipe pile (1), wherein copper belt type sensor cables (2) are correspondingly welded on both sides of the steel pipe pile (1) along an axis direction; each sensor cable is sequentially covered with an epoxy adhesive (5), gold foil paper (6) and an angle steel (7) welded on the steel pipe pile (1) by using the copper belt type sensor cable as a center; a fiber core in each copper belt type sensor cable (2) is transferred into a high-strength armored optical cable (4) with a special fixture and then is led out; and the high-strength armored optical cable (4) is connected with a Brillouin optical fiber demodulator (3).

2. A construction method of the stress-strain testing system for the large-diameter steel pipe pile of the offshore wind turbine of claim 1, comprising the following steps:

a. marking lines for laying copper belt type sensor cables (2) on both sides of a steel pipe pile (1) along an axis direction, polishing a surface of the steel pipe pile (1) along the lines and cleaning dust;

b. laying the copper belt type sensor cables (2) on the polished surface of the steel pipe pile (1), and fixing with an electric welding machine in a fixed-point manner, c. covering the copper belt type sensor cables (2) with an epoxy adhesive (5), standing for 24 hours to firmly bond the copper belt type sensor cables (2) and the steel pipe pile (1), pasting gold foil paper (6) on the surface of the epoxy adhesive after the epoxy adhesive (5) is completely cured;

d. welding an angle steel (7) on the surface of the steel pipe pile (1) by using the copper belt type sensor cable (2) as a center;

e. transferring a fiber core in each copper belt type sensor cable (2) into a high-strength armored optical cable (4) with a special fixture and leading out; and connecting the armored cable with a Brillouin optical fiber demodulator (3); and f. calibrating a sensor through the Brillouin optical fiber demodulator (3), obtaining signal transmitting time by measuring a phase difference generated when a signal is transmitted and received, and calculating a length change of the copper belt type sensor cables (2) so as to obtain a stress value of the steel pipe pile (1).

* * * * *